United States Patent
Torres et al.

(10) Patent No.: US 6,762,017 B2
(45) Date of Patent: Jul. 13, 2004

(54) CONTROL FOR COMPLETE BLOOD COUNT ANALYSIS SYSTEM

(75) Inventors: Richard Torres, East Haven, CT (US); Robert A. Levine, 31 Pilgrim La., Guilford, CT (US) 06437; Stephen C. Wardlaw, Highrock, Lyme, CT (US) 06371

(73) Assignees: Robert A. Levine, Guilford, CT (US); Stephen C. Wardlaw, Lyme, CT (US)

(*) Notice: Subject to any disclaimer, the term of this patent is extended or adjusted under 35 U.S.C. 154(b) by 199 days.

(21) Appl. No.: 10/053,946

(22) Filed: Jan. 24, 2002

(65) Prior Publication Data

US 2003/0138463 A1 Jul. 24, 2003

(51) Int. Cl.$^7$ ................................................ G01N 31/00
(52) U.S. Cl. ...................... 435/2; 435/4; 436/8; 436/16; 600/368
(58) Field of Search .................. 436/16, 8; 435/2, 435/4; 600/368

(56) References Cited

U.S. PATENT DOCUMENTS 4,774,965 A * 10/1988 Rodriguez et al.
5,811,303 A * 9/1998 Ryan

* cited by examiner

Primary Examiner—Leon B. Lankford, Jr.
(74) Attorney, Agent, or Firm—William W. Jones

(57) ABSTRACT

A non-animal based mixture of components serves as a control for complete blood count (CBC) analysis instruments and paraphernalia. The centrifugible non-animal based mixture simulates blood, and contains blood cell-simulating and other blood constituent-simulating components which are present in the mixture in controlled and known amounts. The mixture can be gravimetrically separated into its blood constituent-simulating components so as to serve as a control that simulates a centrifuged blood sample, and is thus used to check the accuracy of CBC blood analysis instruments, such as those marketed by Becton Dickinson and Company, under the trademark "QBC".

16 Claims, 1 Drawing Sheet

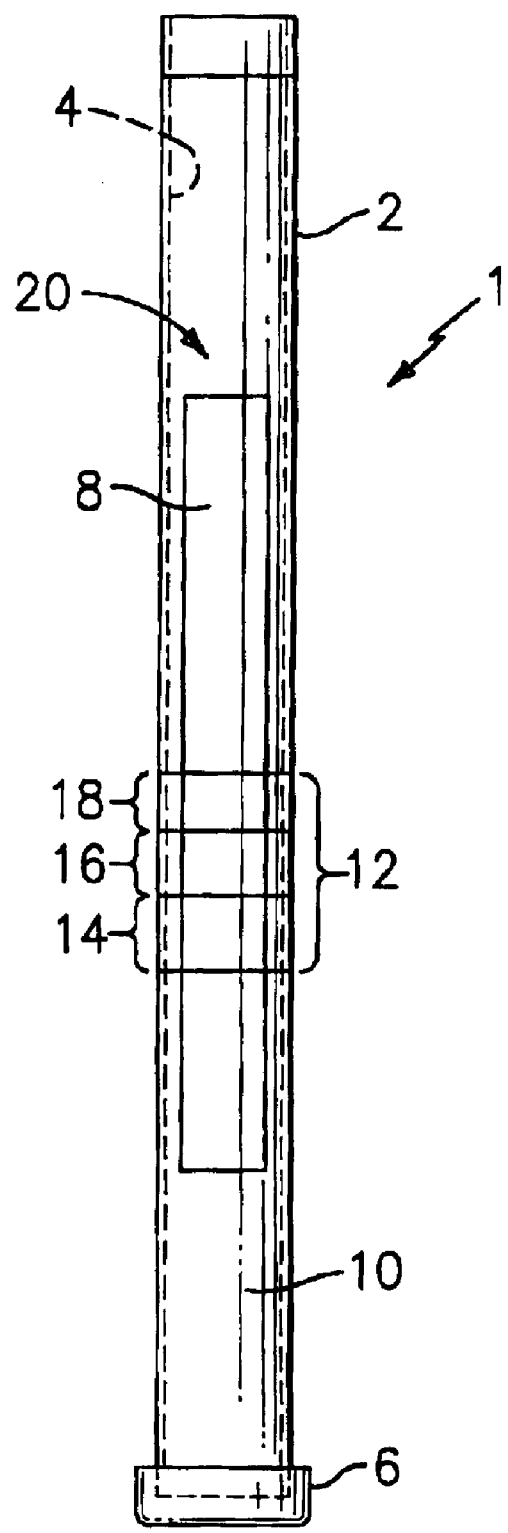

CONTROL FOR COMPLETE BLOOD COUNT ANALYSIS SYSTEM

TECHNICAL FIELD

This invention relates to a non-animal based mixture of chemical and physical elements that serves as a control for a quantitative buffy coat analysis which is performed in accordance with the patented "QBC" paraphernalia. More particularly, this invention relates to a centrifugible non-animal based mixture which simulates blood, and which contains blood cell and other constituent-equivalent components in known amounts, which mixture can be gravimetrically separated into its blood constituent-equivalent components so as to be used as a control which simulates blood and which can be used for checking the accuracy of blood analysis instruments, which instruments are marketed by Becton Dickinson and Company under the trademark "QBC".

BACKGROUND ART

Quantitative buffy coat ("QBC") analysis is a technique utilized for measurement of hematologic parameters which include a plastic insert or float disposed in a capillary tube. Values for hematocrit, platelets, hemoglobin concentration, total white blood cell count, percent granulocytes, and percent lymphocytes and monocytes can be derived from measurements of layers that develop in the "QBC" tube during centrifugation of anticoagulated whole blood. U.S. Pat. Nos. 6,262,799; 5,889,584; 5,888,184; 5,830,639; 5,132,087; 4,940,668; 4,695,553; 4,594,165; 4,567,754; 4,137,755; 4,091,659; 4,082,085; 4,077,396; and 4,027,660 relate to the "QBC" technology in general and are incorporated herein in their entirety.

Quality control is a fundamental component of clinical laboratory practice. It is critical for ensuring the validity of analytical results and, as such, is an area of focus of regulatory agencies. In the "QBC" technology field, given the fact that the accuracy of the expansion of the buffy coat layer, and its constituents, is a function of the float diameter and the tube bore diameter, the control must be able to confirm that the platelet layer, the granulocyte and lymphocyte/monocyte layers, and the total white blood cell layer are being accurately measured.

The ideal "QBC" control must thus confirm the accuracy of the following parameters: 1) that the sample mixing and tube filling technique, i.e. the fill meniscus and hematocrit are correct; 2) that the height of the various cell layers referred to above are correct; 3) that the float density is correct; and 4) that the sensing mechanism and software used by the reader to detect and measure the height of the different colored and fluorescent bands affecting the buffy coat parameters are correct.

A "QBC" hematology control is described in U.S. Pat. No. 5,811,303 granted Sep. 22, 1998 to Wayne L. Ryan. The "QBC" hematology control is presently being marketed by Streck Laboratories of Minneapolis, Minn. The Streck control consists of: a red cell part having fixed mammalian red blood cells; a granulocyte component made from stained and fixed mammalian granulocytes; a lymphocyte/monocyte component also made from variably fixed mammalian granulocytes; a polystyrene latex bead component for the platelet component; and an isotonic saline suspension media with approximately twelve chemical additives. Several aspects of the Streck Laboratories composition make it adequate, but less than ideal. The separation, fixation, and staining processes are costly and time consuming, and chemical additives are necessary for ensuring the stability and proper sedimentation of the layers, thus adding to the cost and complexity. Furthermore, the animal basedal basis of the mixture is responsible for its relatively short stability and a significant variability of results. In particular, significant degradation has been observed about one week after shipment and unpredictability in results has been observed relating to the different mammalian sources of the animal based components of the control, and the varying efficiency of the processing steps, such as fixation.

It would be highly desirable to provide a "QBC" control substance having the following characteristics, i.e.,: it would remain a stable emulsion after mixing for at least two minutes prior to being placed in a "QBC" tube; it would be stable for shipping for at least sixty days after preparation, preferably at ambient temperatures; it would be non-hazardous to humans during preparation and use; it would be low cost and relatively simple to manufacture; it would be easy to use requiring nothing more than simple mixing; and it would be stable, after opening, using, and reclosing, for at least one week. The control mixture of the present invention provides all of the aforesaid desirable characteristics.

DISCLOSURE OF THE INVENTION

We have devised an anticoagulated whole blood-simulating control mixture that solves the aforementioned problems and that provides the aforementioned desirable characteristics. The control mixture of this invention includes a combination of fluorescent and/or otherwise colored beads having different densities and/or sizes and/or surface chemistries, since the density, size and the surface chemistry of the beads each or all in any combination can contribute to the degree of separation of the beads in the centrifuged control mixture. The beads are preferably combined in the mixture with a suitable number of generally immiscible liquid phases which have different densities and which phases are made into an essentially stable emulsion at 1 g.

The emulsion preferably includes one or more surfactants that will cause the liquid phases to separate into defined regions in the tube when the emulsion is centrifuged in the sample tube. The regions in the tube into which the liquid constituents gravitate will correspond to the plasma layer region and the red cell layer region in an anticoagulated whole blood sample which is centrifuged in the same type of tube. In addition to the liquid constituents in the control mixture, the mixture also includes three types of beads which are present in known amounts, and which are differentiated by color, size and/or density from each other. There will be an uppermost bead layer which simulates the platelet layer in a centrifuged sample of blood; a second medial bead layer which simulates the leukocyte/monocyte layer of the blood's buffy coat; and a third lowermost bead layer which simulates the granulocyte layer in the blood's buffy coat.

The granulocyte-simulating bead layer will preferably have a higher affinity for the liquid phase which simulates the red cell layer than for the other liquid phase which simulates the plasma layer in the centrifuged control. Thus, in descending order in the centrifuged control mixture, the less dense liquid forms the uppermost layer (plasma); the least dense and largest diameter bead group forms the uppermost formed component layer (platelets) in the simulated buffy coat; the medial density and medial diameter bead group forms the medial formed component layer (lymphocytes/monocytes) in the simulated buffy coat; the most dense and smallest diameter bead group forms the lowermost formed component layer (granulocytes) in the simulated buffy coat; and the most dense liquid constituent forms the red cell layer in the simulated blood sample.

It is therefore an object of this invention to provide a non-animal based emulsion of immiscible liquids and bead sets which will simulate the various components of centrifuged anticoagulated whole blood when the emulsion is centrifuged in a blood analysis tube.

It is a further object of this invention to provide an emulsion of the character described wherein the immiscible liquids simulate the plasma and red cell components of the whole blood.

It is another object of this invention to provide an emulsion of the character described wherein the bead sets simulate the components of a centrifuged white cell layer in whole blood.

It is an additional object of this invention to provide an emulsion of the character described wherein the bead sets and liquids are present in the emulsion in controlled amounts so as to enable the emulsion to be used as a control to verify the accuracy of an instrument which is used to determine complete blood counts in centrifuged blood samples.

BRIEF DESCRIPTION OF THE DRAWINGS

These and other objects and advantages of the invention will become more readily apparent from the following detailed description of at least one embodiment of the invention when taken in conjunction with the accompanying drawings wherein:

FIG. 1 is a side elevational view of a blood analysis tube which includes an insert that physically expands the cellular components of the buffy coat in a centrifuged sample of anticoagulated whole blood, which tube contains the control emulsion of this invention.

DETAILED DESCRIPTION OF SPECIFIC EMBODIMENTS OF THE INVENTION

Referring now to FIG. 1, there is shown the results of centrifuging the liquid/bead mixture control emulsion of this invention in a "QBC" blood sampling tube and insert assembly, which assembly is denoted generally by the numeral 1. The assembly 1 includes a tube 2 having a bore 4 in which an insert 8 is positioned. The bottom of the tube 2 is closed by a closure cap 6. The insert 8 has a specific gravity or density which will enable it to float on the most dense constituent of the anticoagulated whole blood sample, as described in the aforesaid prior art. When the assembly 1 is filled with the control emulsion of this invention, and the emulsion is centrifuged in the assembly 1, the emulsion will separate into discrete layers which are described in greater detail below, which layers simulate the various components of centrifuged whole blood. In one embodiment of the invention, the layers 10 and 20 are formed by two respectively immiscible liquid components of the emulsion and simulate the red cell and plasma layers respectively of a centrifuged whole blood sample. The layer 12 which is formed of groups 14, 16 and 18 of different size and density beads, simulates the buffy coat of a centrifuged sample of anticoagulated whole blood, with the layers 14, 16 and 18 simulating the granulocyte, lymphocyte/monocyte, and platelet layers respectively in a centrifuged sample of anticoagulated whole blood. The liquids and beads can be differentially colored so as to be recognizable by an automated instrument which is used to perform a CBC by means of the "QBC" technique.

The liquid layers 20 and 10 can be any mutually immiscible liquids with densities that bracket the maximum and minimum bead densities in the layers 14 and 18 and which allow the insert 8 to gravitate during centrifugation to a location in the tube 2 which is approximately midway between the two liquid layers 10 and 20. For example, an aliphatic alcohol such as decanol with a density of less than 1.000 g/cc could serve as the layer 20, while water with enough salt dissolved in it to bring its density to approximately 1.200 g/cc could be the more dense layer 10. Alternatively lipiodol alone, or in combination with a lower density oil (such as peanut oil) in which lipiodol is miscible, may serve as the more dense layer 10. In one embodiment of the invention, the more dense liquid layer 10 can consist of water with dissolved sodium diatrizoate to a density of about 1.18 g/cc with a added preservative such as 0.5% sodium azide, and the less dense liquid layer 20 is made of low viscosity low fluorescence clear immersion oil such as that produced under the trademark "RESOLVE" by Richard Allan Scientific, of Kalamazoo, Mich. with a density of about 0.92 g/cc. In this configuration, the lipid layer is larger than the non-lipid layer, which means that surfactants should be chosen which are capable of producing a water-in-oil emulsion. In these cases a low hydrophilic-lipophilic balance (HLB) surfactant is typically desirable. "MERPOL SE" a strong surface active compound produced by Dow Chemical, has been observed to be effective in this role. Addition of another surfactant with a higher HLB by the common name of "TWEEN 20" has been experimentally determined to aid in the separation of the bead layers during centrifugation, presumably by acting as a buffer preventing bead to bead clumping in the mixture. A short chain alcohol such as ethanol may serve as a co-surfactant and aid in the creation of a micro emulsion. Sucrose may play a similar role or may be used as an alternative to sodium diatrizoate in increasing the water density. The density of both liquid layers 10 and 20 can be selected so as to enable use of the depth to which the insert 8 sinks into the layer 10 as an indicator of the hemoglobin count in the simulated blood sample.

In one embodiment of the invention, the uppermost bead layer 18 which simulates the platelet layer in the blood's buffy coat can consist of red fluorescent hydrophobic polyvinyl toluene microspheres having a density of approximately 1.027 g/cc and a diameter of approximately 3–7 μm and which microspheres are preferably larger than the other two bead layers described hereinafter. Any manner of coloring the beads (including fluorescence) can be achieved such as through integration of a dye during the bead manufacturing process, or by surface attachment of the dye, and the like. The second bead layer 16 which simulates the lymphocyte/monocyte layer of the blood's buffy coat 12 can consist of 3–5 μm diameter green fluorescent polystyrene latex beads. The beads in the second bead layer 16 can have a polymer density of approximately 1.050 g/cc. The third bead layer 14 which simulates the granulocyte layer in the blood's buffy coat can be formed from red fluorescing 0.5–3 μm diameter carboxylated polystyrene latex beads having a density of about 1.060 g/cc and having a higher affinity for liquid phase 10 which simulates the red cell layer over the other liquid phase 20 which simulates the plasma layer in a centrifuged sample of anticoagulated whole blood.

In the same way that, despite being of similar densities, larger particle layers settle atop layers of smaller particles on the ocean floor, making bottom layer beads smaller than the other two will aid in separation of the bead layers. Thus, the preferred configuration may include decreasing sized beads with increasing density. However, the acceptable size range for all bead layers is limited to between approximately 200 nm and 30 μm. If made too large, the beads will not fit well within the float-capillary wall space. If made too small, the beads will not settle according to density because they are proportionally heavily affected by Brownian motion.

Since the cost of fluorescent beads is significantly higher than the cost of undyed beads, the cost of all fluorescent bead layers can be significantly reduced by making each bead layer a mixture of undyed and dyed beads, essentially diluting the concentration of fluorescent beads in each layer. The correct signal will be produced as long as the beads are of equivalent size, density, and surface chemistry so that they will intermix evenly, or a different combination of size, density, and surface chemistry that will result in even distribution of the fluorescent beads in only that layer. Additionally, a fluorescent bead with a wide emission spectrum may be used in combination with dyed non-fluorescent beads that effectively acts as a filter to tailor the emitted light to the required reader specifications. For example, DNA and RNA covered beads that fluoresce in the red and the green region when mixed with acridine orange, may be combined with red non-fluorescent beads that will filter the emitted light under fluorescence that will be detected as more red than green by the instrument. Dilution of fluorescent beads to about 10% of beads in a layer appears to produce enough signal to allow distinction of a layer in the Becton Dickinson and Company "QBC" "STAR" system.

The densities of the three different bead layers 14, 16 and 18 can also be obtained by utilizing different plastics and plastic mixtures during manufacturing. For example, using a certain percentage of acrylic, vinyltoluene, or divinylbenzene in polystyrene will create beads of varying densities. Polymethyl methacrylate may also be used, producing beads with densities of about 1.12 g/cc.

The general principles that are important relative to the bead layers 14, 16 and 18 are:
1) maintaining the bead diameters between 0.5 and 20 μm, preferably with the less dense beads being of a larger size;
2) using beads with surface carbonyl, amine or other groups substituted for sulfate groups, so that the more polar or tonically active groups are closer to the hydrophilic phase; and
3) maintaining bead density differences to 0.005 g/cc or higher in order to ensure proper separation. The choice of surface chemistry will also affect the surfactant choices outlined below. Other non-animal based elements, including, but not limited to, polymer beads, glass or mineral particles, and plant-derived particles such as pollen, may be used as a substitute for, or in combination with, the fluorescent beads without deviating significantly from the spirit of the invention.

It will be appreciated that it is the thickness of the layers 10, 14, 16, 18 and 20 that enables the mixture to be used as a blood sample-simulating control which can measure the accuracy of an instrument which is used to analyze actual blood samples. Thus the mixture of liquids and particles or beads will contain amounts of the respective components of appropriate densities so as to simulate a blood sample having known CBC values. For example, the mixture can simulate a sample of anticoagulated whole blood which has a hematocrit of 46; a hemoglobin of 15; a granulocyte count of 6,000; a lymphocyte/monocyte count of 2,000; and a platelet count of 200,000. The aforesaid values are merely illustrative of one control mixture that could be used to check the accuracy of the instrument in question. Alternatively, several control mixtures could be used, one of which simulates high end values of the aforesaid CBC components, and another one that simulates low end values of the aforesaid CBC components, and perhaps another one that simulates medial values of the aforesaid CBC components.

All of the components of the mixture are premeasured and are premixed and stored at room temperature or under refrigeration. Stability of the mixture should be on the order of months to years. Since there may be some separation during storage, the mixture will preferably be such that it can form an emulsion with inversion or shaking, which emulsion will be stable for at least two minutes, but preferably about five minutes which is enough time to load the mixture into the "QBC" tube assembly 1. The solution can be loaded by capillary action or with a manual pipette familiar to "QBC" users. A red dye soluble only in the lower liquid layer can be included to make the solution look like blood. The mixture can be handled and manufactured safely. Once loaded, the "QBC" tube is centrifuged and read either by a manual reader or by an automated photodetector.

The potassium oxalate concentration in a "QBC" tube can be accounted for by adjusting the density of the lowermost liquid layer in the mixture so that the float depth in the lowermost liquid layer can be indicative of the hemoglobin in an actual blood sample which is reacted with potassium oxalate. The acridine orange concentration in a "QBC" tube is accounted for by the total fluorescence which is detected in the plasma, platelet and white blood cell layers in the blood sample. Although anti-glycophorin activity, anti-glycophorin being an antibody which is typically in a "QBC" tube which is operative to agglomerate the red cells in the sample, is not currently tested by existing control solutions being used, it may be accounted for, if desired, using this control mixture by coating the lowest density beads with glycophorin and adding colored (e.g. red fluorescing), small (approximately 500 nm), dense (slightly more dense than the lowermost liquid phase) beads that will bind these lower layer beads in the presence of anti-glycophorin (which is an antibody disposed in the commercial "QBC" to agglomerate red cells), but will sink to the bottom of the tube when the amount of anti-glycophorin in the tube is less than the control amount. Without a control amount of functional anti-glycophorin, the lower (i.e. granulocyte) bead layer will be smaller and there will be red fluorescence above the bottom cap of the tube. The particulate layers can also be made from non-fluorescent beads with surfaces that contain exposed DNA or RNA which fluoresce green and red respectively when intercolated by acridine orange which is found in control "QBC" tubes. These nucleic acids will be intercolated by the acridine orange dye in the "QBC" tube. The desired coloring effect, thus identifying the acridine orange concentration in the "QBC" tube.

Since many changes and variations of the disclosed embodiments of the invention may be made without departing from the inventive concept, it is not intended to limit the invention otherwise than as required by the appended claims.

What is claimed is:

1. A mixture of non-animal based components for use as a blood-simulating control for checking the accuracy of complete blood count (CBC) analysis instruments and complete blood count analysis centrifuge tubes, said mixture comprising:
   a) a first liquid component which simulates red blood cells in a blood sample;

b) at least one artificial particulates component which is less dense than said first liquid component and which simulates at least one buffy coat component in a blood sample;

c) a second liquid component which is less dense than each of said first liquid component and said particulates component and which simulates plasma in a blood sample, said second liquid component being immiscible with said first liquid component; and d) said mixture being convertible into a homogeneous emulsion which simulates an anticoagulated whole blood sample.

2. The mixture of claim 1 wherein the emulsion gravimetrically separates into its individual component layers when the emulsion is centrifuged in one of the CBC analysis centrifuge tubes.

3. The mixture of claim 1 wherein each of said mixture components are present in the mixture in predetermined amounts which amounts correlate to components of a predetermined CBC.

4. The mixture of claim 1 wherein said artificial particulates component includes several different microspheres components and wherein individual microspheres in each of said microspheres components are sized differently from the individual microspheres in each of the other microspheres components so as to facilitate gravimetric settling of the microspheres components by size as well as by density.

5. The mixture of claim 4 wherein the microspheres in each of the microspheres components are differentially colored.

6. The mixture of claim 1 wherein the liquid components are differentially colored.

7. The mixture of claim 1 further comprising one or more surfactants which enhance gravimetric separation of the several components in the mixture.

8. The mixture of claim 1 further comprising one or more surfactants which facilitate formation of a gravimetrically separable emulsion which emulsion can be prepared by simple inversion of the mixture.

9. A mixture of non-animal based components for use as a blood-simulating control for checking the accuracy of complete blood count (CBC) analysis instruments and CBC analysis centrifuge tubes, said mixture comprising:

a) a first liquid component which simulates red blood cells in a blood sample;

b) a first artificial microspheres component which is less dense than said first liquid component and which simulates granulocytes in a blood sample;

C) a second artificial microspheres component which is less dense than both of said first liquid component and said first microspheres component, and which simulates lymphocytes and monocytes in a blood sample;

d) a third artificial microspheres component which is less dense than each of said first liquid component, said first microspheres component, and said second microspheres component, and which simulates platelets in a blood sample;

e) a second liquid component which is less dense than each of said first liquid component, said first microspheres component, said second microspheres component, and said third microspheres component, and which simulates plasma in a blood sample, said second liquid component being immiscible with said first liquid component; and f) said mixture being convertible into a homogeneous emulsion which simulates an anticoagulated whole blood sample.

10. The mixture of claim 9 wherein the emulsion gravimetrically separates into its individual component layers when the emulsion is centrifuged in one of the CBC analysis centrifuge tubes.

11. The mixture of claim 9 wherein each of said mixture components are present in the mixture in predetermined amounts which amounts correlate to components of a predetermined CBC.

12. The mixture of claim 9 wherein the individual microspheres in each of said microspheres components are sized differently from the individual microspheres in each of the other microspheres components so as to facilitate gravimetric settling of the microspheres components by size as well as by density.

13. The mixture of claim 9 wherein the microspheres in each in each of the microspheres components are differentially colored.

14. The mixture of claim 9 wherein the liquid components are differentially colored.

15. The mixture of claim 9 further comprising one or more surfactants which enhance gravimetric separation of the several components in the mixture.

16. The mixture of claim 9 further comprising one or more surfactants which surfactants facilitate formation of a gravimetrically separatable emulsion which emulsion can be prepared by simple inversion of the mixture.

* * * * *